United States Patent

Wachtler et al.

[11] Patent Number: 5,196,141
[45] Date of Patent: Mar. 23, 1993

[54] 5-OXY-2-PHENYLPYRIDINES, AND A LIQUID-CRYSTALLINE MEDIUM

[75] Inventors: Andreas Wachtler, Griesheim; Volker Reiffenrath, Rossdorf; Reinhard Hittich, Modautal; Thomas Geelhaar, Mainz; Eike Poetsch, Mühltal, all of Fed. Rep. of Germany

[73] Assignee: Merck Patent Gesellschaft Mit Beschrankter Haftung, Darmstadt, Fed. Rep. of Germany

[21] Appl. No.: 598,603

[22] PCT Filed: Aug. 17, 1990

[86] PCT No.: PCT/EP90/01351
§ 371 Date: Oct. 22, 1990
§ 102(e) Date: Oct. 22, 1990

[87] PCT Pub. No.: WO91/02722
PCT Pub. Date: Mar. 7, 1991

[30] Foreign Application Priority Data

Aug. 26, 1989 [DE] Fed. Rep. of Germany ....... 3928264

[51] Int. Cl.$^5$ ................ C09K 19/34; C07D 211/72; G02F 1/13
[52] U.S. Cl. ................ 252/299.61; 546/301; 359/104
[58] Field of Search ........ 252/299.61, 299.63, 252/299.01; 546/301; 359/104

[56] References Cited

U.S. PATENT DOCUMENTS

| | | | |
|---|---|---|---|
| 4,684,477 | 8/1987 | Sugimori et al. | 252/299.61 |
| 4,795,587 | 1/1989 | Ohno et al. | 252/299.61 |
| 4,876,026 | 10/1989 | Saito et al. | 252/299.61 |
| 4,913,837 | 4/1990 | Gray et al. | 252/299.61 |
| 5,030,383 | 7/1991 | Scheuble et al. | 252/299.61 |
| 5,055,221 | 10/1991 | Scheuble et al. | 252/299.61 |
| 5,055,222 | 10/9991 | Ohno et al. | 252/299.61 |

FOREIGN PATENT DOCUMENTS 2161808 1/1986 United Kingdom.

Primary Examiner—Robert L. Stoll
Assistant Examiner—Philip Tucker
Attorney, Agent, or Firm—Millen, White, Zelano and Branigan

[57] ABSTRACT

The invention relates to 5-oxy-2-phenylpyridines of the formula I

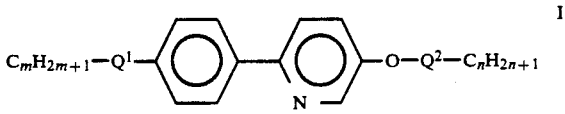

in which
m and n, independently of one another, are each from 1 to 18,
$Q^1$ is —O—, trans-1,4-cyclohexylene, 1,4-phenylene or a single bond, and
$Q^2$ is —CO—,

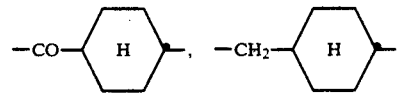

or a single bond,
with the provisos that in the case where $Q^1=Q^2=$a single bond, the sum of $m+n \geq 11$, and in the case where $Q^2=CO$, the radical $C_nH_{2n+1}$ is straight-chain, and to ferroelectric liquid-crystalline media containing these compounds.

2 Claims, No Drawings

5-OXY-2-PHENYLPYRIDINES, AND A LIQUID-CRYSTALLINE MEDIUM

The invention relates to 5-oxy-2-phenylpyridines of the formula I

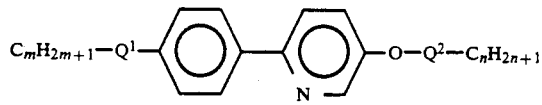

in which m and n, independently of one another, are each from 1 to 18, $Q^1$ is —O—, trans-1,4-cyclohexylene, 1,4-phenylene or a single bond, and $Q^2$ is —CO—,

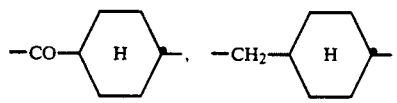

or a single bond,
with the provisos that a) in the case where $Q^1=Q^2=$ a single bond, the sum of $m+n \geq 11$, and b) in the case where $Q^2=CO$, the radical $C_nH_{2n+1}$ is straight-chain, and to ferroelectric liquid-crystalline media containing these compounds.

Chiral, tilted, smectic, liquid-crystalline media having ferroelectric properties can be prepared by adding a suitable chiral dope to base mixtures having one or more tilted smectic phases (L. A. Beresnev et al., Mol. Cryst. Liq. Cryst. 89, 327 (1982); H. R. Brand et. al., J. Physique 44 (lett.), L 771 (1983). Media of this type can be used as dielectrics for rapidly switching displays based on the principle of SSFLC technology described by Clark and Lagerwall (N. A. Clark and S. T. Lagerwall, Appl. Phys. Lett. 36, 899 (1980); U.S. Pat. 4,367,924) on the basis of the ferroelectric properties of the chiral, tilted medium. In these media, the long molecules are arranged in layers, the molecules having a tilt angle to the layer perpendiculars. On moving from layer to layer, the tilt direction changes by a small angle with respect to an axis perpendicular to the layers, thus forming a helical structure. In displays based on the principle of SSFLC technology, the smectic layers are arranged perpendicular to the plates of the cell. The helical arrangement of the tilt directions of the molecules is suppressed by a very small separation of the plates (about 1-2 μm). The longitudinal axes of the molecules are therefore forced to arrange themselves in a plane parallel to the plates of the cell, thus causing two preferred tilt orientations. By applying a suitable electrical alternating field, it is possible to switch back and forth between these two states in the liquid-crystalline phase exhibiting spontaneous polarization. This switching process is considerably faster than in customary twisted cells (TN-LCDs) based on nematic liquid crystals.

A great disadvantage for many applications of the currently available materials having chiral, tilted, smectic phases (such as, for example, Sc*, but also $S_H$*, $S_I$*, $S_J$*, $S_K$*, $S_G$*, $S_F$*) is their low chemical, thermal and photostability. A further disadvantageous property of displays based on currently available chiral, tilted, smectic media is that the values for the spontaneous polarization are too low, which means that the switching time behaviour of the displays is adversely affected and/or the pitch and/or the tilt and/or the viscosity of the media does not conform to the requirements of display technology. In addition, the temperature range of the ferroelectric media is usually too small and is predominantly at excessively high temperatures.

It has now been found that the use of compounds of the formula I as components of chiral, tilted, smectic media can essentially reduce the disadvantages mentioned. The compounds of the formula I are thus preeminently suitable as components of chiral, tilted, smectic liquid-crystalline media. In particular, they can be used to prepare chiral, tilted, smectic liquid-crystalline media which are particularly stable chemically and have favourable ferroelectric phase ranges, favourable values for the viscosity, in particular having broad Sc* phase ranges, excellent supercoolability down to temperatures of less than 0° C. without crystallization occurring, and spontaneous polarization values which are high for phases of this type. P is the spontaneous polarization in $nC/cm^2$. However, the compounds of the formula I are also suitable for liquid-crystalline media for the electroclinic effect.

The compounds of the formula I have a broad field of application. Depending on the choice of substituents, these compounds can be used as base materials from which liquid-crystalline, smectic media are predominantly composed; however, it is also possible to add compounds of the formula I to liquid-crystalline base materials from other classes of compounds in order, for example, to vary the dielectric and/or optical anisotropy and/or the viscosity and/or the spontaneous polarization and/or the phase ranges and/or the tilt angle and/or the pitch of a medium of this type.

GB 2,161,808 gives a very broad general formula for nematic phenylpyridines for use in multiplex cells which covers some of the compounds of the formula I claimed here. However, GB 2,161,808 does not contain any indication of Sc phases for compounds of this type; rather, the compounds described therein are said to be nematic and to have excellent miscibility with other nematic liquid crystals. Specifically, the following compounds are mentioned:

2-(p-pentylphenyl)-5-butyloxypyridine, C→I 38° C., I→S 34° C.

2-(p-butylphenyl)-5-ethoxypyridine, C→I 29.5° C.

2-(p-pentylphenyl)-5-propyloxypyridine, C→I 42° C.

2-(p-hexylphenyl)-5-butyloxypyridine, C→S 26° C., S→I 44.5° C.

In view of the good miscibility with other nematic liquid crystals, the unidentified smectic phases described for two of these compounds cannot be Sc, but instead, for example, are $S_B$.

JP 63/165,344 discloses optically active phenylpyridines of the formula

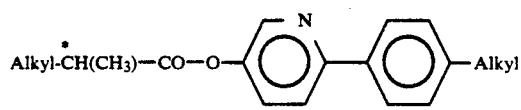

However, these compounds are not suitable as achiral base materials for ferroelectric liquid-crystalline media, but instead are employed as dopes.

It is thus not possible for a person skilled in the art to deduce from the prior art that the compounds according to the invention have predominantly broad and favourably located Sc phases and are distinguished by favourable values for the rotation viscosity. The invention thus relates to the 5-oxy-2-phenylpyridines of the formula I.

The invention furthermore relates to ferroelectric, liquid-crystalline media containing at least one compound of the formula I, and to liquid-crystal displays, in particular ferroelectric, electrooptical displays, which contain media of this type.

The media according to the invention preferably contain at least two, in particular at least three, compounds of the formula I. Particular preference is given to chiral, tilted, smectic liquid-crystalline phases according to the invention whose achiral base mixture contains, in addition to compounds of the formula I, at least one other component having negative or low positive dielectric anisotropy. This (these) further component(s) of the achiral base mixture may make up from 1 to 50%, preferably from 10 to 25%, of the base mixture. Suitable further components having low positive or negative dielectric anisotropy are compounds of the formula IV, which formula covers the compounds of the sub-formulae IVa to IVi

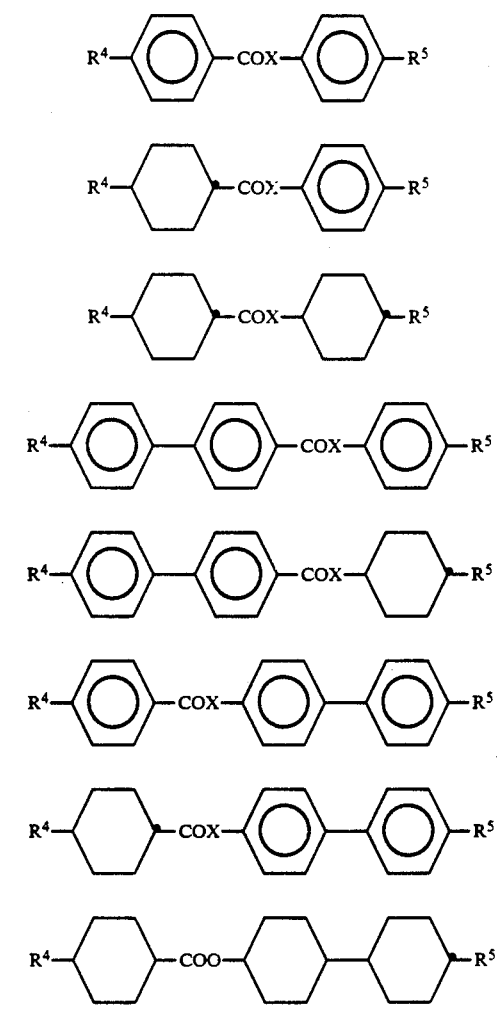

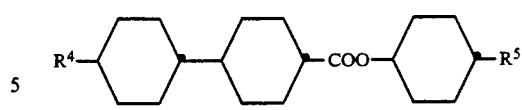

$R^4$ and $R^5$ are each preferably straight-chain alkyl, alkoxy, alkanoyloxy or alkoxycarbonyl, in each case having from 3 to 12 C atoms. X is preferably O. In the compounds of the formulae IVa, IVb, IVd, IVe, IVf and IVg, one 1,4-phenylene group may also be laterally substituted by halogen or CN, in particular preferably by fluorine.

Particular preference is given to the compounds of the sub-formulae IVa, IVb, IVd and IVf in which $R^4$ and $R^5$ are each straight-chain alkyl or alkoxy, in each case having from 5 to 10 C atoms.

Particularly preferred individual compounds are indicated in Table I below:

TABLE I

| Formula | $R^4$ | $R^5$ | X |
|---|---|---|---|
| IVa | n-Decyloxy | n-Heptyloxy | O |
| IVa | n-Hexyloxy | n-Decyloxy | O |
| IVa | n-Octyloxy | n-Heptyl | O |
| IVa | n-Octyloxy | n-Pentyl | O |
| IVa | n-Decyloxy | n-Heptyl | O |
| IVa | n-Decyloxy | n-Pentyl | O |
| IVf | n-Pentyl | n-Pentyl | O |
| IVf | n-Pentyl | n-Hexyl | O |

The compounds of the sub-formulae IVc, IVh and IVi are suitable as additives for reducing the melting point and are normally added to the base mixtures in an amount of not more than 5%, preferably from 1 to 3%. In the compounds of the sub-formulae IVc, IVh and IVi, $R^4$ and $R^5$ are preferably straight-chain alkyl having from 2 to 7, preferably from 3 to 5, C atoms. A further class of compounds which is suitable for reducing the melting point in the phases according to the invention is that of the formula

in which $R^4$ and $R^5$ have the preferred meaning given for IVc, IVh and IVi.

Suitable further components having negative dielectric anisotropy are also compounds containing the structural element A, B or C.

 A

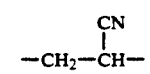 B

 C

Preferred compounds of this type conform to the formula Va, Vb or Vc:

 Va

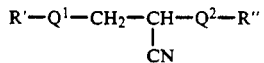 Vb

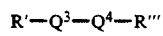 Vc

R' and R" are each preferably straight-chain alkyl or alkoxy groups, in each case having from 2 to 10 C atoms. $Q^1$ and $Q^2$ are each 1,4-phenylene, trans-1,4-cyclohexylene, 4,4'-biphenylyl, 4-(trans-4-cyclohexyl)-phenyl or trans,trans-4,4'-bicyclohexyl, or one of the groups $Q^1$ and $Q^2$ is alternatively a single bond.

$Q^3$ and $Q^4$ are each 1,4-phenylene, 4,4'-biphenylyl or trans-1,4-cyclohexylene. One of the groups $Q^3$ and $Q^4$ may alternatively be 1,4-phenylene in which at least one CH group has been replaced by N. R''', is an optically active radical containing an asymmetric carbon atom of the structure $$\begin{array}{cc} \overset{Cl}{|} & \overset{CN}{|} \\ -CH^*- & \text{or} \quad -CH^*-. \end{array}$$

Particularly preferred compounds of the formula Vc are those of the formula Vc':

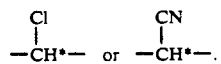 Vc' in which A is 1,4-phenylene or trans-1,4-cyclohexylene, and n is 0 or 1.

The compounds of the formula I cover the preferred dinuclear and trinuclear materials given below.

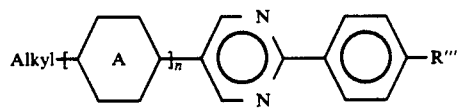 Ia in which m is preferably from 7 to 12, and n is from 6 to 12.

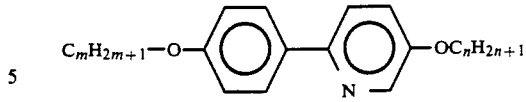 Ib in which n and m, independently of one another, are each preferably from 5 to 12.

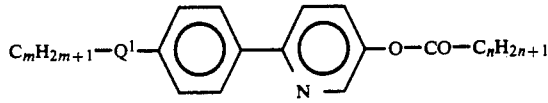 Ic in which the radical $C_nH_{2n+1}$ is straight-chain, and $Q^1$ is preferably —O— or a single bond, and m and n, independently of one another, are each from 5 to 12.

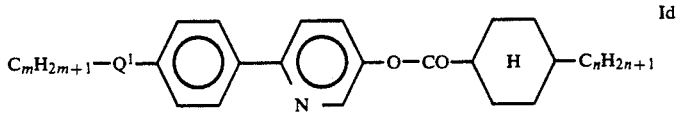 Id in which $Q^1$ is preferably —O— or a single bond, m is preferably from 5 to 12, and n is preferably from 2 to 12.

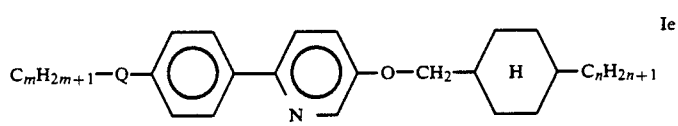 Ie in which Q is preferably —O— or a single bond, m is preferably from 5 to 12, and n is preferably from 2 to 12.

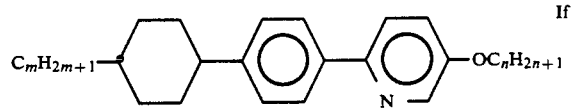 If in which m is preferably from 2 to 12, and n is from 2 to 12.

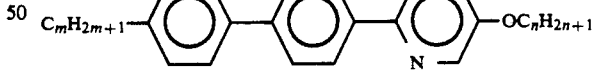 Ig in which m is preferably from 3 to 12, and n is from 2 to 12.

Of these, those of the sub-formulae Ia and Ib, in particular Ib, are particularly preferred.

m is preferably from 5 to 14, in particular from 6 to 12. n is preferably from 3 to 12. The radicals $C_mH_{2m+1}$ and $C_nH_{2n+1}$ are preferably straight-chain. Compounds of the formula I containing relatively short radicals of this type are also suitable as components of nematic media (n and m, independently of one another, are 1 to 7).

$Q^1$ is preferably —O—.

The compounds of the formula I are prepared by methods which are known per se, as described in the literature (for example in the known works such as Houben-Weyl, Methoden der Organishen Chemie [Methods of Organic Chemistry], Georg-Thieme-Verlag, Stuttgart).

If desired, the starting materials can also be formed in situ by not isolating them from the reaction mixture, but instead immediately reacting them further to form the compounds of the formula I.

The compounds according to the invention can easily be prepared in accordance with the reaction schemes below.

Scheme 1

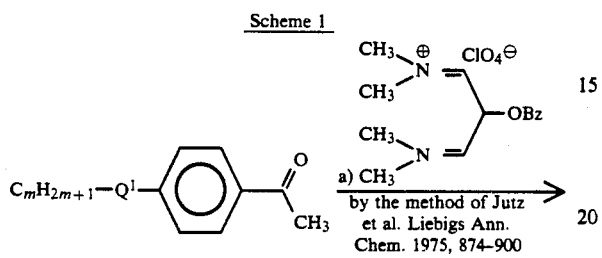

Scheme 2

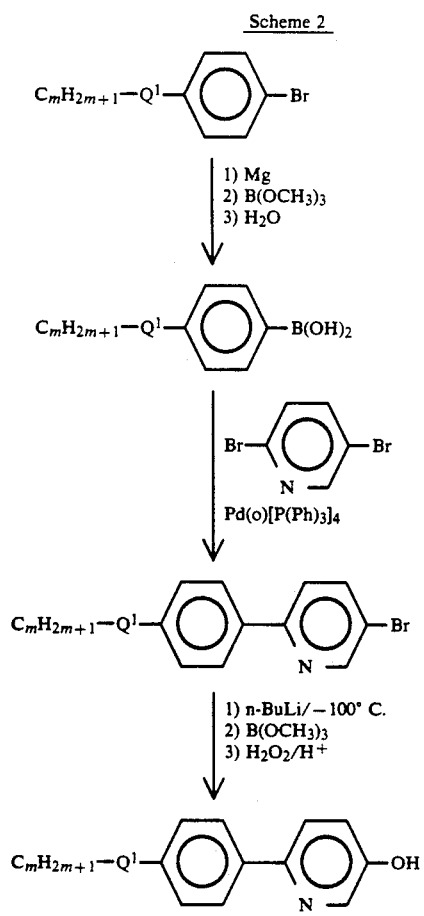

-continued
Scheme 2

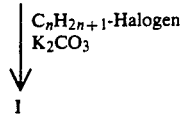

Scheme 3

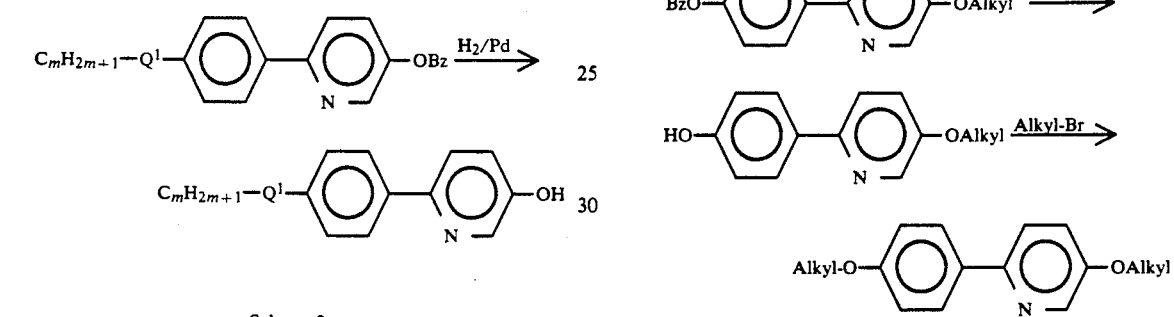

The compounds according to the invention can also be obtained by coupling organometallic zinc compounds with appropriate bromopyridine derivatives in accordance with DE-OS 3,632,410.

The synthesis of some particularly important hydroxyl intermediates is described below:
a) 5-Hydroxy-2(4-alkylphenyl)pyridines and 5-hydroxy-2-(4-alkoxyphenyl)pyridines can be obtained from the 2-benzyloxytrimethinium salt by condensation with 4-alkyl- or 4-alkoxyacetophenones, reaction with NH$_3$/NH$_4$Cl or ammonium acetate in analogous manner to the procedure of C. Jutz et al. (Liebigs Ann. Chem. 1975 874–900) and subsequent hydrogenolysis, or from 4-alkyl- or 4-alkoxyphenylboric acid by coupling with 5-acetoxy-2-bromopyridine (obtainable from 5-hydroxy-2-bromopyridine by esterification) in the presence of a Pd catalyst in corresponding manner to the work of Suzuki et al. (Synth. Commun. 11, 513–19 (1981)).
b) 5-Alkoxy-2(4-hydroxyphenyl)pyridines can be obtained by coupling 4-benzyloxyphenylboric acid with 5-alkoxy-2-bromopyridine in corresponding manner to the abovementioned literature, with subsequent hydrogenolysis.

The liquid-crystalline media according to the invention preferably contain 2 to 40, in particular 4 to 30, components as further constituents besides one or more compounds according to the invention. These media very particularly preferably contain 7 to 25 components besides one or more compounds according to the invention. These further constituents are preferably selected from nematic or nematogenic (monotropic or isotropic) substances, in particular substances from the classes of the azoxybenzenes, benzylideneanilines, biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid and of cyclohexylcyclohexanecarboxylic acid, phenylcyclohexanes, cyclohexylbiphenyls, phenylcyclohexylcyclohexanes, cyclohexylcyclohexanes, cyclohexylcyclohexenes, cyclohexylcyclohexylcyclohexenes, 1,4-bis-cyclohexylbenzenes, 4,4'-bis-cyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)ethanes, 1-cyclohexyl-2-biphenylylethanes, 1-phenyl-2-cyclohexylphenylethanes, optionally halogenated stilbenes, benzyl phenyl ethers, tolans and substituted cinnamic acids. The 1,4-phenylene groups in these compounds may also be fluorinated.

The most important compounds suitable as further constituents of media according to the invention can be characterized by the formulae 1, 2, 3, 4 and 5:

|                          |   |
|--------------------------|---|
| R'—L—E—R"                | 1 |
| R'—L—COO—E—R"            | 2 |
| R'—L—OOC—E—R"            | 3 |
| R'—L—CH$_2$CH$_2$—E—R"   | 4 |
| R'—L—C≡C—E—R"            | 5 |

In the formulae 1, 2, 3, 4 and 5, L and E, which may be identical or different, are in each case, independently of one another, a divalent radical from the group formed by -Phe-, -Cyc-, -Phe-Phe-, -Phe-Cyc-, -Cyc-Cyc-, -Pyr-, -Dio-, -G-Phe- and -G-Cyc- and their mirror images, where Phe is unsubstituted or fluorine-substituted 1,4-phenylene, Cyc is trans-1,4-cyclohexylene or 1,4-cyclohexenylene, Pyr is pyrimidine-2,5-diyl or pyridine-2,5-diyl, Dio is 1,3-dioxane-2,5-diyl and G is 2-(trans-1,4-cyclohexyl)ethyl, pyrimidine-2,5-diyl, pyridine-2,5-diyl or 1,3-dioxane-2,5-diyl.

One of the radicals L and E is preferably Cyc, Phe or Pyr. E is preferably Cyc, Phe or Phe-Cyc. The media according to the invention preferably contain one or more components selected from the compounds of the formulae 1, 2, 3, 4 and 5 in which L and E are selected from the group comprising Cyc, Phe and Pyr and simultaneously one or more components selected from the compounds of the formulae 1, 2, 3, 4 and 5 in which one of the radicals L and E is selected from the group comprising Cyc, Phe and Pyr and the other radical is selected from the group comprising -Phe-Phe-, -Phe-Cyc-, -Cyc-Cyc-, -G-Phe- and -G-Cyc-, and optionally one or more components selected from the compounds of the formulae 1, 2, 3, 4 and 5 in which the radicals L and E are selected from the group comprising -Phe-Cyc-, -Cyc-Cyc-, -G-Phe- and -G-Cyc-.

In the compounds of the sub-formulae 1a, 2a, 3a, 4a and 5a, R' and R" are in each case, independently of one another, alkyl, alkenyl, alkoxy, alkenyloxy or alkanoyloxy having up to 8 carbon atoms. In most of these compounds, R, and R" are different from one another, one of these radicals usually being alkyl or alkenyl. In the compounds of the sub-formulae 1b, 2b, 3b, 4b and 5b, R" is —CN, —CF$_3$, F, Cl or —NCS; in this case, R has the meaning given for the compounds of the sub-formulae 1a to 5a and is preferably alkyl or alkenyl. However, other variants of the proposed substituents in the compounds of the formulae 1, 2, 3, 4 and 5 are also common. Many such substances or alternatively mixtures thereof are commercially available. All these substances can be obtained by methods which are known from the literature or analogously thereto.

Besides components from the group comprising the compounds 1a, 2a, 3a, 4a and 5a (Group 1), the media according to the invention also preferably contain components from the group comprising the compounds 1b, 2b, 3b, 4b and 5b (Group 2), whose proportions are preferably as follows:

Group 1: 20 to 90%, in particular 30 to 90%,
Group 2: 10 to 80%, in particular 10 to 50%,
the sum of the proportions of the compounds according to the invention and of the compounds from Groups 1 and 2 adding up to 100%.

The media according to the invention preferably contain 1 to 40%, in particular preferably 5 to 30%, of compounds according to the invention. Further preferred media are those which contain more than 40%, in particular 45 to 90%, of compounds according to the invention. The media preferably contain three, four or five compounds according to the invention.

The media according to the invention are prepared in a manner which is customary per se. In general, the components are dissolved in one another, expediently at elevated temperature. By means of suitable additives, the liquid-crystalline phases can be modified in accordance with the invention in a manner such that they can be used in all types of liquid-crystal display elements which have hitherto been disclosed. Additives of this type are known to those skilled in the art and are described in detail in the literature (H. Kelker/R. Hatz, Handbook of Liquid Crystals, Verlag Chemie, Weinheim, 1980). For example, pleochroic dyes can be added for the production of coloured guest-host systems, or substances can be added to modify the dielectric anisotropy, the viscosity and/or the orientation of the nematic phases.

The examples below are intended to illustrate the invention without representing a limitation. mp.=melting point, cp.=clear point. Above and below, percentages are per cent by weight; all temperatures are indicated in degrees Celsius. "Customary work-up" means that water is added, the mixture is extracted with methylene chloride, the organic phase is separated off, dried and evaporated, the product is purified by crystallization and/or chromatography.

In addition, the abbreviations have the following meanings: C: crystalline-solid state, S: smectic phase (the index characterizes the phase type), N: nematic state, Ch: cholesteric phase, I: isotropic phase. The number between two symbols indicates the conversion temperature in degrees Celsius.

EXAMPLE 1

0.1 mol of 2-(4-nonylphenyl)-5-hydroxypyridine (prepared by condensation of 4-nonylacetophenone with 2-benzyloxytrimethinium perchlorate by the method of Jutz et al. (see page 11) with subsequent hydrogenolysis of the benzyl ether) is etherified using 0.11 mol of 1-bromoheptane and 0.11 mol of potassium carbonate in dimethyl formamide as solvent. After work-up, the 2-(4-nonylphenyl)-5-heptyloxypyridine is recrystallized from isopropanol.

Analogous reaction of 4-benzyloxyacetophenone with 2-octyloxytrimethinium perchlorate, ammonium acetate and hydrogenolytic cleavage of the benzyl ether gives 2-(4-hydroxyphenyl)-5-octyloxypyridine, which is alkylated using 1-bromodecane to give 2-(4-n-decyloxyphenyl)-5-octyloxypyridine.

EXAMPLES 2 TO 204

The following compounds of the formula I are prepared analogously or by etherification or esterification of corresponding hydroxyl compounds by standard methods:

| | Sub-formula | m | n | $Q^1$ |
|---|---|---|---|---|
| (2) | Ia | 7 | 6 | |
| (3) | Ia | 7 | 7 | |
| (4) | Ia | 7 | 8 | |
| (5) | Ia | 7 | 9 | |
| (6) | Ia | 7 | 10 | |
| (7) | Ia | 7 | 11 | |
| (8) | Ia | 7 | 12 | |
| (9) | Ia | 8 | 6 | |
| (10) | Ia | 8 | 7 | |
| (11) | Ia | 8 | 8 | |
| (12) | Ia | 8 | 9 | |
| (13) | Ia | 8 | 10 | |
| (14) | Ia | 8 | 11 | |
| (15) | Ia | 8 | 12 | |
| (16) | Ia | 9 | 6 | |
| (17) | Ia | 9 | 7 | |
| (18) | Ia | 9 | 8 | |
| (19) | Ia | 9 | 9 | |
| (20) | Ia | 9 | 10 | |
| (21) | Ia | 9 | 11 | |
| (22) | Ia | 9 | 12 | |
| (23) | Ia | 10 | 6 | |
| (24) | Ia | 10 | 7 | |
| (25) | Ia | 10 | 8 | |
| (26) | Ia | 10 | 9 | |
| (27) | Ia | 10 | 10 | |
| (28) | Ia | 10 | 11 | |
| (29) | Ia | 10 | 12 | |
| (30) | Ia | 11 | 6 | |
| (31) | Ia | 11 | 7 | |
| (32) | Ia | 11 | 8 | |
| (33) | Ia | 11 | 9 | |
| (34) | Ia | 11 | 10 | |
| (35) | Ia | 11 | 11 | |
| (36) | Ia | 11 | 12 | |
| (37) | Ia | 12 | 6 | |
| (38) | Ia | 12 | 7 | |
| (29) | Ia | 12 | 8 | |
| (40) | Ia | 12 | 9 | |
| (41) | Ia | 12 | 10 | |
| (42) | Ia | 12 | 11 | |
| (43) | Ia | 12 | 12 | |
| (44) | Ib | 6 | 6 | |
| (45) | Ib | 6 | 7 | |
| (46) | Ib | 6 | 8, K 89 $S_c$ 104 N 105 I | |
| (47) | Ib | 6 | 9 | |
| (48) | Ib | 6 | 10 | |
| (49) | Ib | 6 | 11 | |
| (50) | Ib | 6 | 12 | |
| (51) | Ib | 8 | 6 | |
| (52) | Ib | 8 | 7 | |
| (53) | Ib | 8 | 8, K 77 $S_c$ 109 I | |
| (54) | Ib | 8 | 9 | |
| (55) | Ib | 8 | 10 | |
| (56) | Ib | 8 | 11 | |
| (57) | Ib | 8 | 12 | |
| (58) | Ib | 9 | 6 | |
| (59) | Ib | 9 | 7 | |
| (60) | Ib | 9 | 8 | |
| (61) | Ib | 9 | 9 | |
| (62) | Ib | 9 | 10 | |
| (63) | Ib | 9 | 11 | |
| (64) | Ib | 9 | 12 | |
| (65) | Ib | 10 | 6 | |
| (66) | Ib | 10 | 7 | |
| (67) | Ib | 10 | 8, K 70 ($S_x$ 68) $S_c$ 111 I | |
| (68) | Ib | 10 | 9 | |
| (69) | Ib | 10 | 10 | |
| (70) | Ib | 10 | 11 | |
| (71) | Ib | 10 | 12 | |
| (72) | Ib | 11 | 6 | |
| (73) | Ib | 11 | 7 | |
| (74) | Ib | 11 | 8 | |
| (75) | Ib | 11 | 9 | |
| (76) | Ib | 11 | 10 | |
| (77) | Ib | 11 | 11 | |
| (78) | Ib | 11 | 12 | |
| (79) | Ib | 12 | 6 | |
| (80) | Ib | 12 | 7 | |
| (81) | Ib | 12 | 8 | |
| (82) | Ib | 12 | 9 | |
| (83) | Ib | 12 | 10 | |
| (84) | Ib | 12 | 11 | |
| (85) | Ib | 12 | 12 | |
| (86) | Ic | 8 | 8 | —'—' |
| (87) | Ic | 8 | 7 | —'—' |
| (88) | Ic | 9 | 7 | —'—' |
| (89) | Ic | 8 | 8 | —O— |
| (90) | Ic | 8 | 7 | —O— |
| (91) | Ic | 9 | 7 | —O— |
| (92) | Ic | 10 | 7 | —O— |
| (93) | Id | 8 | 3 | —'—' |
| (94) | Id | 8 | 4 | —'—' |
| (95) | Id | 8 | 5 | —'—' |
| (96) | Id | 8 | 6 | —'—' |
| (97) | Id | 8 | 7 | —'—' |
| (98) | Id | 8 | 8 | —'—' |
| (99) | Id | 8 | 9 | —'—' |
| (100) | Id | 9 | 3 | —'—' |
| (101) | Id | 9 | 4 | —'—' |
| (102) | Id | 9 | 5 | —'—' |
| (103) | Id | 9 | 6 | —'—' |
| (104) | Id | 9 | 7 | —'—' |
| (105) | Id | 9 | 8 | —'—' |
| (106) | Id | 9 | 9 | —'—' |
| (107) | Id | 10 | 3 | —'—' |
| (108) | Id | 10 | 4 | —'—' |
| (109) | Id | 10 | 5 | —'—' |
| (110) | Id | 10 | 6 | —'—' |
| (111) | Id | 10 | 7 | —'—' |
| (112) | Id | 10 | 8 | —'—' |
| (113) | Id | 10 | 9 | —'—' |
| (114) | Id | 11 | 3 | —'—' |
| (115) | Id | 11 | 4 | —'—' |
| (116) | Id | 11 | 5 | —'—' |
| (117) | Id | 11 | 6 | —'—' |
| (118) | Id | 11 | 7 | —'—' |
| (119) | Id | 11 | 8 | —'—' |
| (120) | Id | 11 | 9 | —'—' |
| (121) | Id | 8 | 3 | —O— |
| (122) | Id | 8 | 4 | —O— |
| (123) | Id | 8 | 5 | —O— |
| (124) | Id | 8 | 6 | —O— |
| (125) | Id | 8 | 7 | —O— |
| (126) | Id | 8 | 8 | —O— |
| (127) | Id | 8 | 9 | —O— |
| (128) | Id | 9 | 3 | —O— |
| (129) | Id | 9 | 4 | —O— |
| (130) | Id | 9 | 5 | —O— |
| (131) | Id | 9 | 6 | —O— |
| (132) | Id | 9 | 7 | —O— |
| (133) | Id | 9 | 8 | —O— |
| (134) | Id | 9 | 9 | —O— |
| (135) | Id | 10 | 3 | —O— |
| (136) | Id | 10 | 4 | —O— |
| (137) | Id | 10 | 5 | —O— |
| (138) | Id | 10 | 6 | —O— |
| (139) | Id | 10 | 7 | —O— |
| (140) | Id | 10 | 8 | —O— |
| (141) | Id | 10 | 9 | —O— |
| (142) | Id | 11 | 3 | —O— |
| (143) | Id | 11 | 4 | —O— |
| (144) | Id | 11 | 5 | —O— |
| (145) | Id | 11 | 6 | —O— |
| (146) | Id | 11 | 7 | —O— |
| (147) | Id | 11 | 8 | —O— |
| (148) | Id | 11 | 9 | —O— |

-continued

| Sub-formula | m | n | $Q^1$ |
|---|---|---|---|
| (149) Ie | 8 | 3 | '—' |
| (150) Ie | 8 | 4 | '—' |
| (151) Ie | 8 | 5 | '—' |
| (152) Ie | 8 | 6 | '—' |
| (153) Ie | 8 | 7 | '—' |
| (154) Ie | 8 | 8 | '—' |
| (155) Ie | 8 | 9 | '—' |
| (156) Ie | 9 | 3 | '—' |
| (157) Ie | 9 | 4 | '—' |
| (158) Ie | 9 | 5 | '—' |
| (159) Ie | 9 | 6 | '—' |
| (160) Ie | 9 | 7 | '—' |
| (161) Ie | 9 | 8 | '—' |
| (162) Ie | 9 | 9 | '—' |
| (163) Ie | 10 | 3 | '—' |
| (164) Ie | 10 | 4 | '—' |
| (165) Ie | 10 | 5 | '—' |
| (166) Ie | 10 | 6 | '—' |
| (167) Ie | 10 | 7 | '—' |
| (168) Ie | 10 | 8 | '—' |
| (169) Ie | 10 | 9 | '—' |
| (170) Ie | 11 | 3 | '—' |
| (171) Ie | 11 | 4 | '—' |
| (172) Ie | 11 | 5 | '—' |
| (173) Ie | 11 | 6 | '—' |
| (174) Ie | 11 | 7 | '—' |
| (175) Ie | 11 | 8 | '—' |
| (176) Ie | 11 | 9 | '—' |
| (177) Ie | 8 | 3 | —O— |
| (178) Ie | 8 | 4 | —O— |
| (179) Ie | 8 | 5 | —O— |
| (180) Ie | 8 | 6 | —O— |
| (181) Ie | 8 | 7 | —O— |
| (182) Ie | 8 | 8 | —O— |
| (183) Ie | 8 | 9 | —O— |
| (184) Ie | 9 | 3 | —O— |
| (185) Ie | 9 | 4 | —O— |
| (186) Ie | 9 | 5 | —O— |
| (187) Ie | 9 | 6 | —O— |
| (188) Ie | 9 | 7 | —O— |
| (189) Ie | 9 | 8 | —O— |
| (190) Ie | 9 | 9 | —O— |
| (191) Ie | 10 | 3 | —O— |
| (192) Ie | 10 | 4 | —O— |
| (193) Ie | 10 | 5 | —O— |
| (194) Ie | 10 | 6 | —O— |
| (195) Ie | 10 | 7 | —O— |
| (196) Ie | 10 | 8 | —O— |
| (197) Ie | 10 | 9 | —O— |
| (198) Ie | 11 | 3 | —O— |
| (199) Ie | 11 | 4 | —O— |
| (200) Ie | 11 | 5 | —O— |
| (201) Ie | 11 | 6 | —O— |
| (202) Ie | 11 | 7 | —O— |
| (203) Ie | 11 | 8 | —O— |
| (204) Ie | 11 | 9 | —O— |

EXAMPLE 205

0.1 mol of 4-(trans-4-pentylcyclohexyl)phenylboric acid is coupled with 0.1 mol of 2,5-dibromopyridine in toluene/2N NaHCO$_3$ solution (1:1) using tetrakis [triphenylphosphine]palladium(0) as a catalyst in accordance with Scheme 2. n-Butyillithium and subsequently trimethylborate are added to the coupling product at $-100°$ C. in THF. 20 ml of a 3% H$_2$O$_2$ solution are added to the boric acid obtained in this way, and the mixture is stirred at room temperature for 2 hours. The resultant 2-[4-(trans-4-pentylcyclohexyl)phenyl]-5-hydroxypyridine is etherified analogously to Example 1 using 1-bromooctane. After work-up, the 2-[4-(trans-4-pentylcyclohexyl)phenyl]-5-octyloxypyridine is recrystallized.

EXAMPLES 206 TO 223

The following compounds of the formula I are prepared analogously.

| Example | Sub-Formula | m | n |
|---|---|---|---|
| (206) | If | 3 | 8 |
| (207) | If | 3 | 9 |
| (208) | If | 3 | 10 |
| (209) | If | 3 | 11 |
| (210) | If | 5 | 2, K 94 N 222 I |
| (211) | If | 5 | 9 |
| (212) | If | 5 | 10 |
| (213) | If | 7 | 8 |
| (214) | If | 7 | 9 |
| (215) | If | 7 | 10 |
| (216) | If | 8 | 8 |
| (217) | If | 8 | 9 |
| (218) | If | 8 | 10 |
| (219) | If | 8 | 6 |
| (220) | Ig | 8 | 8 |
| (221) | Ig | 7 | 8 |
| (222) | Ig | 8 | 6 |
| (223) | Ig | 10 | 10 |

We claim:

1. A ferroelectric liquid-crystalline medium having at least two liquid-crystalline components, wherein said medium contains one or more 5-oxy-2-phenylpyridine compounds of the formula

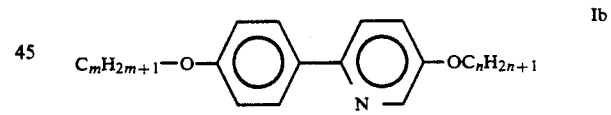

Ib in which n and m, independently of one another, are each from 5 to 12.

2. An electrooptical display containing, as a dielectric, a medium according to claim 1.

* * * * *